United States Patent
Wakabayashi

[11] Patent Number: 5,997,172
[45] Date of Patent: Dec. 7, 1999

[54] AIR-DRIVEN VIBRATOR

[75] Inventor: Toshiaki Wakabayashi, Tokyo, Japan

[73] Assignee: Micron Co., Ltd., Japan

[21] Appl. No.: 09/066,766

[22] Filed: Apr. 28, 1998

[30] Foreign Application Priority Data

May 15, 1997 [JP] Japan ................................... 9-141056

[51] Int. Cl.⁶ .................................................. B01F 11/00
[52] U.S. Cl. ........................................................... 366/124
[58] Field of Search ................................... 366/108, 117, 366/120, 123, 124, 125, 126, 128

[56] References Cited

U.S. PATENT DOCUMENTS

| | | | |
|---|---|---|---|
| 2,422,639 | 6/1947 | Wenander | 366/123 |
| 3,318,163 | 5/1967 | Matson | 366/126 |
| 3,727,890 | 4/1973 | Seidl et al. | 366/123 |
| 4,199,264 | 4/1980 | Uebel | 366/123 |
| 4,427,384 | 1/1984 | Sertich | 366/124 |
| 4,453,919 | 6/1984 | Takeshita | 433/120 |
| 5,190,456 | 3/1993 | Hasegawa | 433/120 |

FOREIGN PATENT DOCUMENTS

| | | |
|---|---|---|
| 0261272 | 3/1988 | European Pat. Off. . |
| 432909 | 9/1967 | Switzerland . |

*Primary Examiner*—Tony G. Soohoo
*Attorney, Agent, or Firm*—Lorusso & Loud

[57] ABSTRACT

The air-driven vibrator (10) includes a disc-shaped vibratory element (40) movably received in a disc-shaped working chamber (38). Upon injecting air jets into the chamber (38) through tangential injection ports (46), the element (40) is rotated and oscillated to generate vibration. The feature of the vibrator is that inwardly directed projections (66, 72) are provided on the inner end faces (34, 36) of the chamber (38) to prevent the element (40) from sticking to the end faces (34,36) when the vibrator is not in use. Due to the provision for the projections (66, 72), the edge of the element (40) need not be chamfered. This enables mass production of the elements (40) and increases the production yield of the elements (40).

20 Claims, 9 Drawing Sheets

$\theta = 88°$

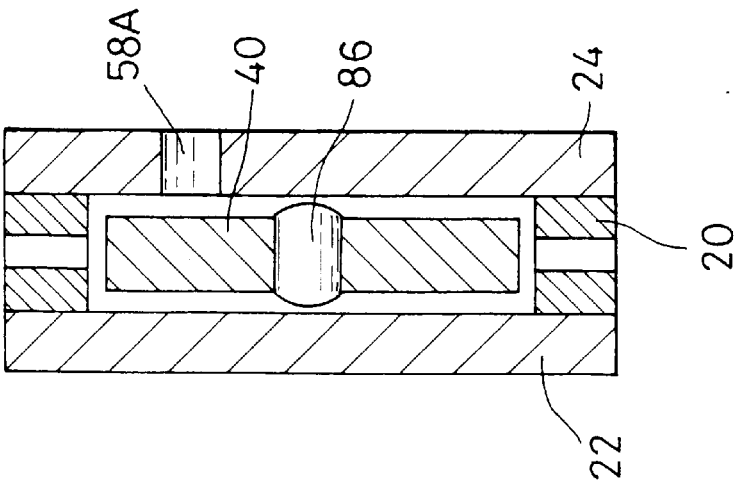
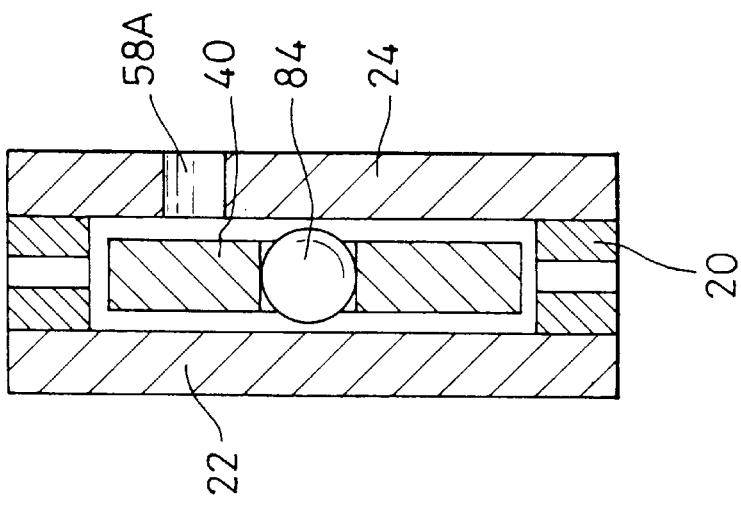
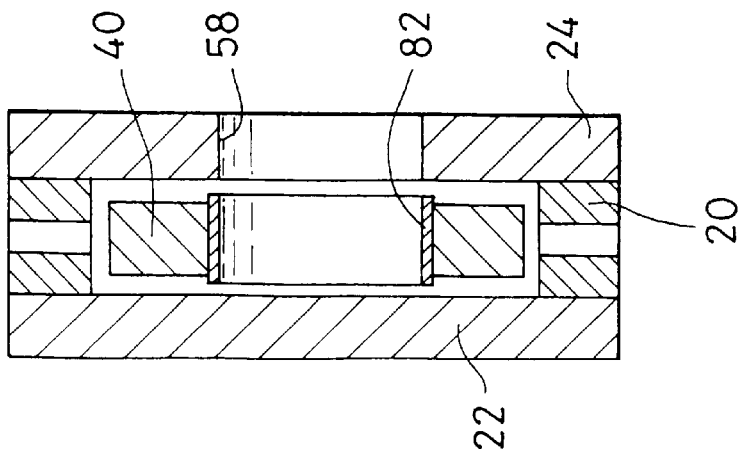

AIR-DRIVEN VIBRATOR

TECHNICAL FIELD

The present invention relates to a vibrator for generating vibration under the action of a working fluid under pressure such as compressed air. More particularly, this invention is concerned with improvements in a vibrator of the type having a disc-shaped vibratory element or vibration generating element.

BACKGROUND ART

U.S. Pat. No. 4,453,919 discloses an air-driven vibrator having a body defining a disc-shaped working chamber in which a disc-shaped vibratory element or rotor made of steel is received for oscillatory movement, a plurality of air injection ports being arranged tangentially to the working chamber to inject compressed air therein to thereby excite the vibratory element, the vibrator further having an exhaust port for discharging used air. The vibrator may be incorporated, for example, in a dental scaler to oscillate a vibratory tool adapted to remove calculus or plaque from teeth.

Although the mechanism of vibration generation taking place in this vibrator is not clear, upon injection of compressed air tangentially into the working chamber to produce a swirling air stream therein, the vibratory element rotates or oscillates like a coin wobblingly spinning on a table surface and strikes the end walls of the working chamber thereby generating vibration.

When after use the supply of compressed air is terminated, the vibratory element, no longer excited, will cease to rotate and will therefore fall vertically downwards within the working chamber under the action of the gravity. The particular part of the wall of the working chamber upon which the vibratory element will finally rest and the angular position in which the vibratory element will finally repose will be dictated by the angular position of the working chamber relative to the vertical.

If, when the vibrator is not operated, the vibrator is held in such a position that the inner end wall of the working chamber lies in a generally horizontal plane so that the vibratory element similarly lying in a substantially horizontal position rests upon the inner end wall of the working chamber, as shown in FIG. 6A of U.S. Pat. No. 4,453,919, there is a risk of the vibratory element to inadvertently adhere to or "stick" to the inner wall of the working chamber as a result of one of the axial end faces of the element being in snug contact with the inner end wall of the chamber.

The risk of the vibratory element to stick will be increased particularly when the vibrator is properly lubricated because a film of lubricant formed and existing between the end face of the element and the inner end wall of the chamber promotes adhesion. Formation of moisture condensate on the inner walls of the working chamber similarly tends to assist sticking.

Furthermore, it is desirable that the end faces of the vibratory element and the inner end walls of the working chamber be finished by a lapping machine in order to enhance the degree of dimensional precision thereof. However, the specular surfaces of the element and chamber walls thus formed by lapping finishing would cause the vibratory element to stick more strongly to the chamber walls.

In the event that the vibratory element once sticks to the inner walls of the working chamber, the vibratory element would not resume its movement merely by reopening the air supply. To restart the vibrator, the vibratory element must be separated or detached away from the inner walls of the working chamber by hammering the vibrator or otherwise giving impact thereon.

U.S. Pat. No. 4,453,919 solved this problem of sticking by conically tapering the axial end faces of the vibratory element at a small angle by chamfering along the circumferential edges of the element, as shown in FIGS. 5A–5H and FIG. 6B thereof, to ensure that the vibratory element is separated from the inner walls of the working chamber by air jets blown into the wedge-shaped space formed between the conical end face of the element and the flat inner wall of the working chamber.

Hitherto, the chamfering of the disc-shaped vibratory elements has been carried out by using a cylindrical grinding machine.

More specifically, a disc-shaped unfinished vibratory element 1 prepared by cutting a steel rod is chucked by a chucking device 2 of a rotary workpiece holder of the cylindrical grinding machine as shown in FIG. 1 of the accompanying drawings, and the axis 3 of the workpiece holder is positioned at an angle, for example, of 88° relative to an axis 5 of a grinder wheel 4 as shown in FIG. 2. Then the vibratory element 1 as chucked by the chuck 2 is translated forward toward the rotating grinder wheel 4 as the element is rotated about the axis 3 of the workpiece holder. In this manner, one of the end faces of the element 1 is ground and chamfered conically at a small angle of 2°.

Then, the semifinished vibratory element is detached from the chuck of the workpiece holder and, after being turned over for 180°, the element is again chucked and ground to chamfer the other end face.

However, the problem encountered in the conventional process for chamfering the vibratory elements is that the vibrators used and incorporated in dental handpieces are so small in size that the axial thickness of the vibratory elements is extremely thin, it being on the order of only 1 mm. Accordingly, it has been difficult to properly chuck the vibratory elements in the workpiece holder of the cylindrical grinding machine. In particular, it has been extremely difficult to chuck those elements having one of the end faces already subjected to chamfering.

Because of the difficulty in properly chucking the vibratory elements, it has often been encountered that the axis of the element as chucked in the chuck is misaligned with the axis of the workpiece holder of the grinding machine. This has precluded to perform chamfering accurately. As a result, a large number of defective elements have been produced so that the production yield of the vibratory elements has been extremely low.

Furthermore, it has been necessary to carry out chamfering of the vibratory elements manually one by one. This has resulted in a fluctuation in the quality of the finished elements, thereby also giving rise to low production yield. In addition, chamfering by manual operation is costly and time consuming and precludes manufacturing by the mass production process.

DISCLOSURE OF THE INVENTION

Accordingly, an object of the present invention is to provide a vibrator of the type described, which does not require chamfering of the vibratory element and which is yet operable without fail whenever injection of compressed air is commenced.

Another object of the invention is to provide a vibrator of the type described, which is free from the problem of sticking of the vibratory element and which is comprised of those component parts which can be manufactured with a high production yield.

A still another object of the invention is to provide a vibrator of the type described, wherein sticking of the vibratory element is effectively prevented and which is easy to manufacture.

A further object of the invention is to provide a vibrator of the type described, which is free from the problem of sticking of the vibratory element and which has a structure that permits manufacture by the mass production process.

Another object of the invention is to provide a vibrator of the type described, which consists of component parts which can be fabricated with a uniformly high quality.

This invention provides a vibrator having a rigid body having a disk-shaped working chamber, a disc-shaped vibratory element received in the chamber for oscillatory movement, means for injecting a working fluid under pressure into the chamber in a tangential direction, and means for exhausting used working fluid out of the chamber. The feature of the invention is that axial end faces of the vibratory element are made substantially flat and that the body is provided with a projection protruding axially inwardly of at least one of the opposite end walls of the chamber. As used herein and in the appended claims, the terms "axially inwardly" and "axially outwardly" refer, respectively, to the axial direction toward and away from the center of the vibrator body.

With this arrangement, the projection provided on the end wall of the chamber serves to prevent the axial end wall of the vibratory element from being brought into close contact with the end wall of the chamber to thereby prevent sticking of the vibratory element when the vibrator is not operated. Due to the provision for the projection, a gap is always secured between the axial end wall of the vibratory element and the end wall of the chamber during the inoperative condition of the vibrator, although the axial end faces of the vibratory element are machined flat. Accordingly, upon commencement of injection of compressed air into the working chamber, the vibratory element is readily put into motion to generate vibration.

Because in this manner the axial end faces of the vibratory element are made flat, chamfering or tapering of the vibratory elements are no longer needed. Therefore, the vibratory elements can be manufactured in an extremely simple manner as compared with the conventional method of manufacture. The elements' axial end faces that are flat may be machined with a high degree of precision by using a planar grinding machine and a lapping machine so that the production yield of the vibratory element is remarkably increased. Furthermore, in contrast with the conventional process wherein the vibratory elements have to be ground manually one by one by the cylindrical grinding machine, planar grinding and lapping operations may be carried out on a batch basis for a large number of workpieces at a time. Accordingly, it is possible to manufacture the vibratory element by a mass production process.

The projection may be made integrally with the inner end wall of the working chamber by any suitable process such as soldering, relieving of the end wall and the like. However, according to a preferred embodiment of the invention, the projection is made separate from the part forming the inner wall of the working chamber. To this end, an end plate defining the inner wall of the working chamber is provided with an axial bore in which an insert member having an extension protruding axially inwardly of the end wall of the chamber is fixed such as by press-fitting.

As in this embodiment the end face of the end plate may be made flat, the end plate may be machined by planar grinding and lapping in a simple manner and with a high degree of accuracy. The insert members may be manufactured separately from the end plates by a mass production process. The end plate and the insert member are readily assembled together in the case that the insert member is mounted in the bore of the end plate by press-fit.

In another embodiment of the invention, the insert member is in the form of a collar having an axial bore which forms part of the exhaust passage. The collar is arranged coaxially with the body of the vibrator. With this arrangement, manufacture and assemblage of the vibrator can be simplified since the collar is fixed by utilizing the exhaust passage. Another advantage is that the collar does not interfere with the vibratory element because it is situated at the center of the body.

In a still another embodiment of the invention, the axial end faces of the vibratory element are made flat and the element is provided with a central bore in which an insert member is inserted in a manner to protrude axially outwardly of the axial end faces of the vibratory element.

These features and advantages of the invention, as well as other features and advantages thereof, will become apparent from the following description.

BRIEF DESCRIPTION OF THE DRAWINGS

FIGS. 11A–11C are cross-sectional views showing the essential parts of the modified forms of the vibrator shown in FIG. 3;

BEST MODE FOR CARRYING OUT THE INVENTION

Figure 1:
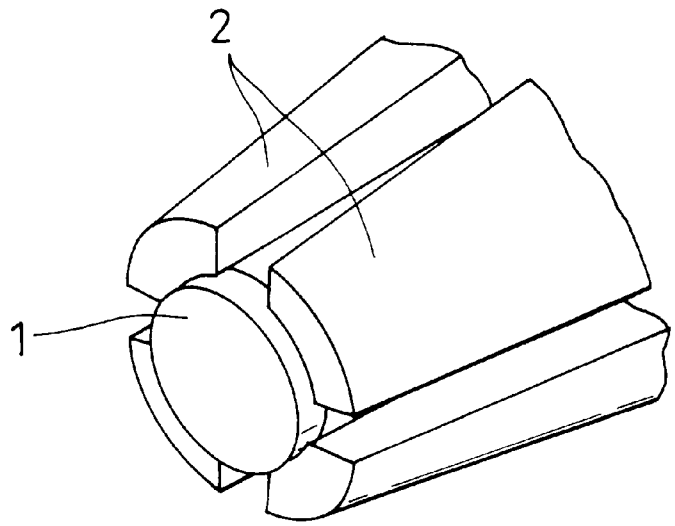
FIGS. 1 and 2 are schematic views illustrating the conventional method of beveling the axial end faces of vibratory elements by using a cylindrical grinding machine.
Figure 2:
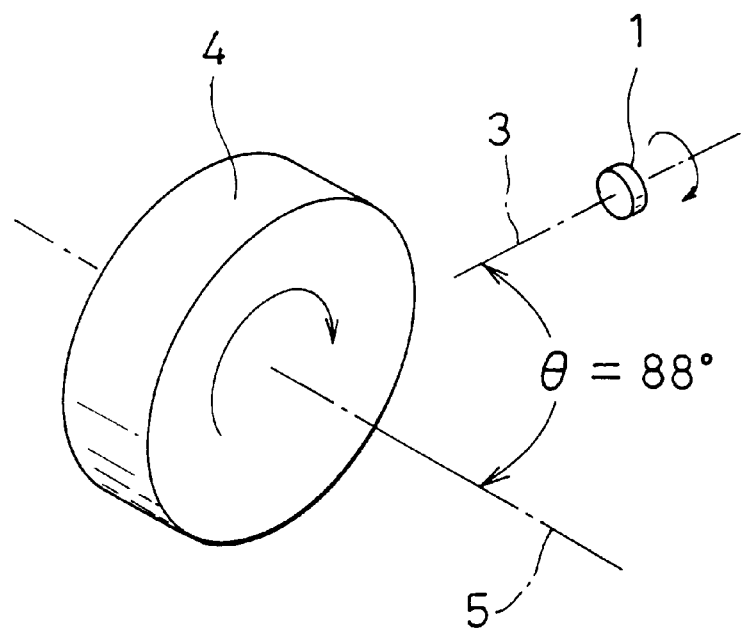
Figure 3:
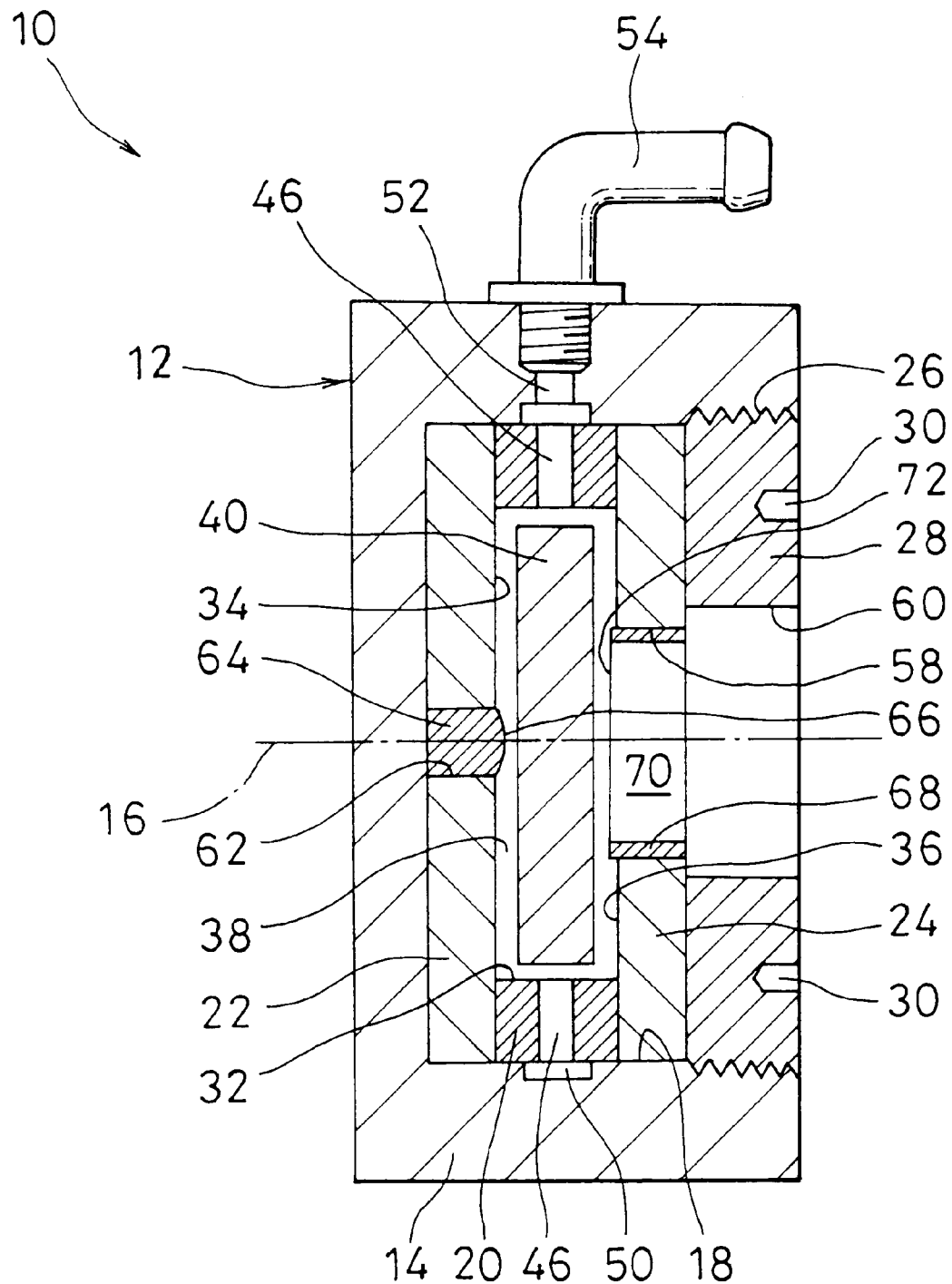
FIG. 3 is an axial cross-sectional view of the vibrator according to the simplest form of the invention, with air injection ports extending tangentially to the working chamber being shown as extending in the radial direction for illustrative purposes.
Figure 4:
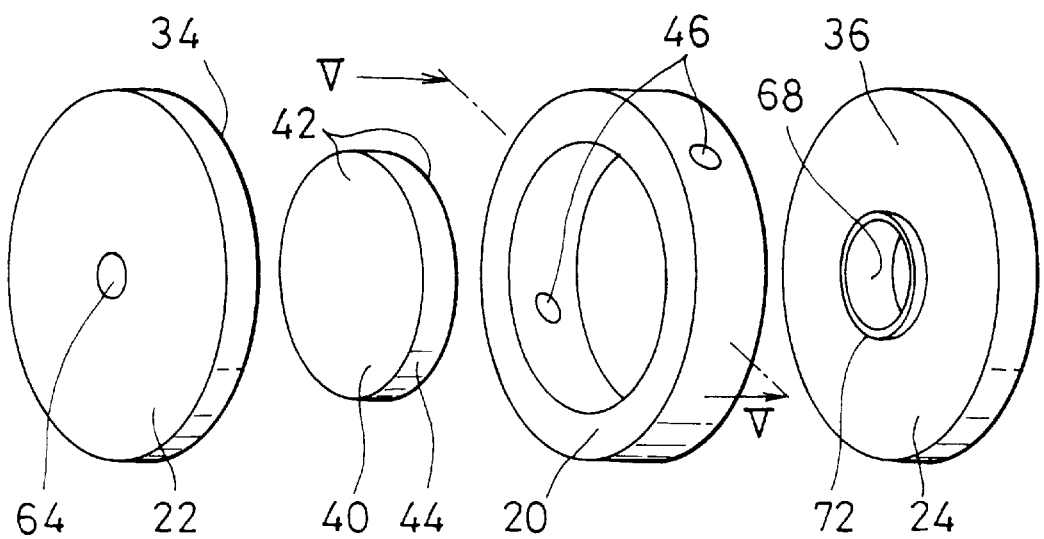
FIG. 4 is an exploded perspective view of the essential parts of the vibrator shown in FIG. 3.
Figure 5:
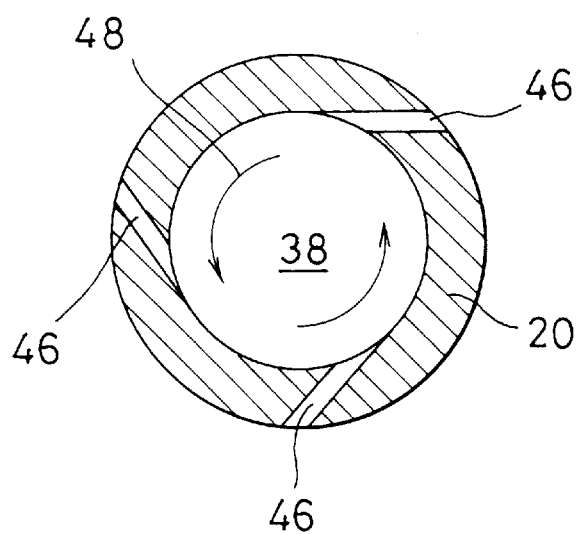
FIG. 5 is a cross-sectional view of an injection ring taken along the line V—V of FIG. 4.

In FIGS. 3–5, there is shown the simplest form of the vibrator according to the invention. Referring to these drawings, the vibrator 10 includes a body 12 made, for example, of steel. In the illustrated embodiment, the body 12 has a cylindrical outer casing 14 in which a bore 18 having an axis 16 is formed. The body 12 further includes a tubular air injection ring 20 arranged coaxially in the bore 18 and a pair of opposite disc-shaped end plates 22 and 24 disposed on both sides of the ring 20.

The injection ring 20 and the end plates 22 and 24 are held together within the outer casing 14 by a threaded retainer 28 screwed into an internal thread 26 of the outer casing 14. The retainer 28 is provided with a pair of diametrically opposite holes 30 designed to be engaged by a spanner.

A disc-shaped working chamber or rotor chamber 38 is defined by the circumferential inner face 32 of the injection ring 20, the inner end face 34 of the end plate 22, and the inner end face 36 of the end plate 24.

A disc-shaped vibratory element or rotor 40 is movably and freely received in the working chamber 38. The vibratory element or vibration generating element 40 is defined by a pair of opposite flat axial end faces 42 and a cylindrical outer face 44.

The axial and radial sizes of the vibratory element 40, respectively, are selected to be slightly smaller than the axial and radial sizes of the working chamber 38 to ensure that the vibratory element 40 is received in the working chamber 38 with a small clearance therebetween.

The vibratory element 40 and the end plates 22 and 24 are preferably made of a highly wear resistant material such as high speed steel. To control the axial thickness with a high degree of precision, it is preferable that, after heat treatment and grinding by a planar grinding machine, the vibratory element 40 as well as the end plates 22 and 24 are subjected to precision machining by a lapping machine to finish the end faces thereof. Preferably, planar grinding and lapping of the vibratory elements 40 and end plates 22 and 24 are carried out on a batch basis for a substantial number of workpieces at a time, so as to ensure that the vibrators are manufactured by a mass production process.

The injection ring 20 are provided with a plurality of injection ports or nozzles 46, numbering three, for example. As will be understood from FIG. 5, the injection ports 46 are open tangentially into the working chamber 38 so as to produce a swirling air stream 48 in the chamber 38.

The outer casing 14 is provided with an annular groove 50 facing the injection ports 46, the groove 50 being in communication with an inlet fitting 54 through a radial port 52.

The inlet fitting 54 may be connected to a source of compressed air through an air hose, not shown. As compressed air is supplied to the inlet fitting 54, air is injected through the injection ports 46 tangentially into the working chamber 38 to thereby generate a swirl of air 48 within the chamber 38.

Figure 6:
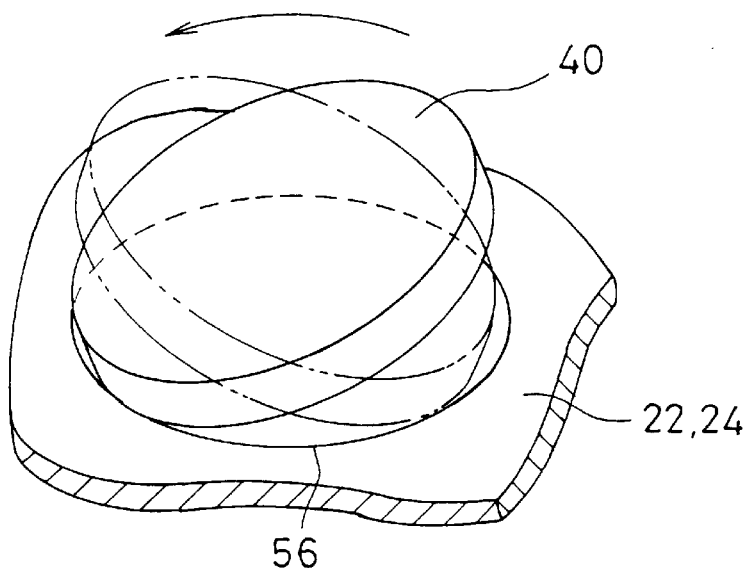
FIG. 6 is a schematic view showing the manner in which a vibratory element generates vibration as it rotates and wobbles.

This causes the vibratory element 40 to rotate in a manner analogous to a coin wobbling and spinning on a surface as illustrated in FIG. 6, thereby striking the end plates 22 and 24 and generating vibration. Such a movement of the vibratory element 40 is confirmed by a circular wear print or track 56 (FIG. 6) formed on the inner end faces 34 and 36 of the end plates 22 and 24.

Used air is discharged to the ambient atmosphere through an exhaust port 58 formed coaxially across the end plate 24 and another exhaust port 60 formed coaxially across the retainer 28, the ports 58 and 60 serving as exhaust means.

Referring again to FIGS. 3 and 4, according to the invention, the end plate 22 is formed with a coaxial bore 62 in which an insert 64 in the form of a short rod is press-fit. As best shown in FIG. 3, the axial length of the insert member 64 is made slightly greater than the axial thickness of the end plate 22 to ensure that the inner end of the insert 64 forms a projection 66 that protrudes from the inner end face 34 of the end plate 22 axially inwardly toward the working chamber 38. The projection 66 serves to prevent the vibratory element 40 from sticking to the inner end face of the end plate 22 when the vibrator is not operated.

In the exhaust port 58 of the end plate 24, on the other hand, there is press-fit an insert 68 in the form of a collar. The collar 68 is provided therethrough with an axial bore 70 which actually serves as an exhaust passage. Similar to the insert 64, the axial length of the collar 68 is made slightly greater than the axial thickness of the end plate 24, so that the annular inner end 72 of the collar 68 projects axially inwardly from the inner face 36 of the end plate 24 into the working chamber 38. Similar to the projection 66, the annular extension 72 of the collar 68 serves as a projection for preventing the vibratory element 40 from sticking to the inner end face of the end plate 24.

To provide a commonality of component parts in the vibrator, the sub-assembly consisting of the end plate 22 and the insert 64 may be made similar to and replaced with the subassembly made of the end plate 24 and the collar 68.

The diameter of the collar 68 must be selected smaller enough than the diameter of the wear print 56 (FIG. 6) of the vibratory element 40 in order to avoid that the element 40 is interfered by the projection 72 as the element is rotated or oscillated.

Similarly, the axial height of the projections 66 and 72 as measured from the inner end faces 34 and 36 of the end plates must be limited such that the projections 66 and 72 would not interfere with the vibratory element 40 as it is moved.

To this end, the axial height of the projections 66 and 72 is preferably precision controlled by subjecting the sub-assembly of the end plate 22 and the insert 64 as well as the sub-assembly of the end plate 24 and the collar 68 to planar grinding followed by lapping. Alternatively, the sub-assemblies may be assembled by first fabricating the inserts 64 and 68 having a precisely controlled axial length and by then press-fitting them into the axial bores of the end plates 22 and 24, respectively.

To describe the mode of use and operation of the vibrator 10, the body 12 of the vibrator may be suitably coupled in a vibration transmitting relationship to an object to be vibrated. As an air hose is connected to the inlet fitting 54 and compressed air is supplied causing air to be injected through the injection ports 46 into the working chamber 38, the vibratory element 40 is rotated and strikes the end plates 22 and 24, as described hereinbefore with reference to FIG. 6, whereby vibration is generated and is transmitted to the object.

During operation, the projections 66 and 72 will not hinder the vibratory or oscillatory movement of the element 40 since the axial height and the radial dimension of the projections 66 and 72 are selected not to interfere with the moving element 40 as described before.

When injection of compressed air is terminated, the vibratory element 40 in the working chamber 38 will fall vertically under the action of the gravity.

Figure 7:
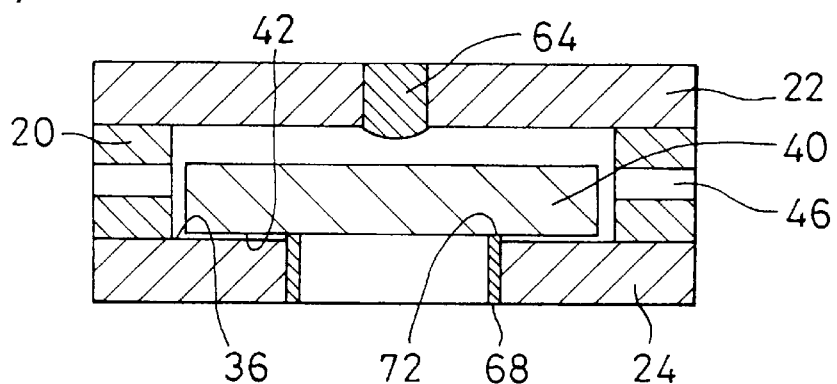
FIGS. 7 and 8 are cross-sectional views of the essential parts of the vibrator shown in FIG. 3, with the vibratory element shown as being in the inoperative position.

If the vibrator 10 not in use is placed in such a position that the end plate 24 is situated underside of the end plate 22, the vibratory element 40 will rest upon the annular projection 72 of the collar 68 as shown typically in FIG. 7. As a result, the axial end face 42 of the element 40 will be spaced away from the inner end face 36 of the end plate 24 by a distance equal to the height of the projection 72. Thus, the projection 72 acts to prevent the axial end face 42 of the element 40 and the inner end face 36 of the end plate 24 from being brought into contact with each other.

When in this condition the supply of compressed air is restarted, air jets will be blown into the narrow gap formed between the axial end face 42 of the element 40 and the inner end face 36 of the end plate 24 to thereby put the vibratory element 40 again into motion without fail.

Figure 8:
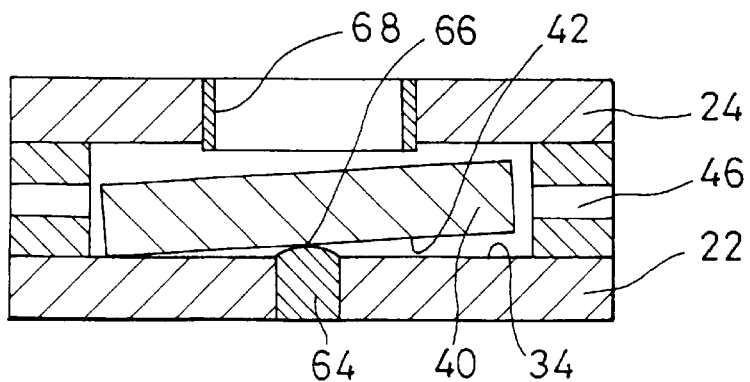

If in the inoperative condition of the vibrator the end plate 22 is situated below the end plate 24 as shown in FIG. 8, the edge of the vibratory element 40, at a given point along the circumference thereof, will be in contact with the inner end face 34 of the plate 22, whereas the region of the edge diametrically opposite to the point of contact will be lifted away from the inner end face 34 due to the presence of the projection 66. Accordingly, when supply of compressed air is resumed, air jets will be blown into the wedge-shaped gap formed between the axial end face 42 of the element 40 and the inner end face 36 of the end plate 24 so that the vibratory element 40 will readily restart its vibratory movement.

Figure 9:
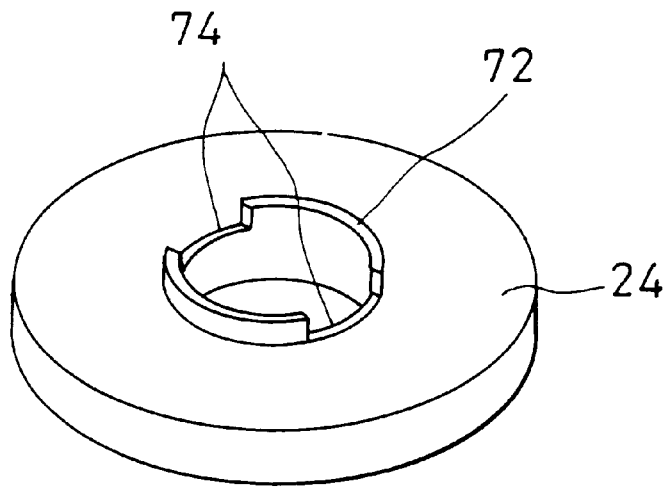
FIG. 9 is a perspective view showing the modified form of the end plate and collar sub-assembly shown in FIG. 3.

FIG. 9 illustrates a modified version of the collar 68 of the end plate 24. In this version, the annular projection 72 of the collar 68 is provided with diametrically opposite cutouts 74. With this arrangement, when injection of compressed air into the working chamber 38 is reopened to restart the vibrator while the vibrator is in the position shown in FIG. 7, used air in the chamber 38 will be smoothly discharged through the cutouts 74 toward the exhaust passage 70. This will assist dusts and powders formed by wear of metallic parts as well as lubricant to be discharged through the cutouts 74 toward the exhaust port thereby achieving self-cleaning of the working chamber.

Figure 10A:
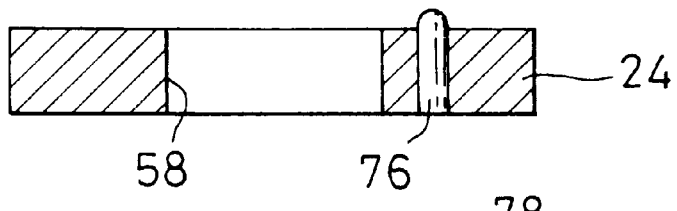
FIGS. 10A–10C are cross-sectional views showing further modified forms of the end plate and collar sub-assembly shown in FIG. 3.
Figure 10B:
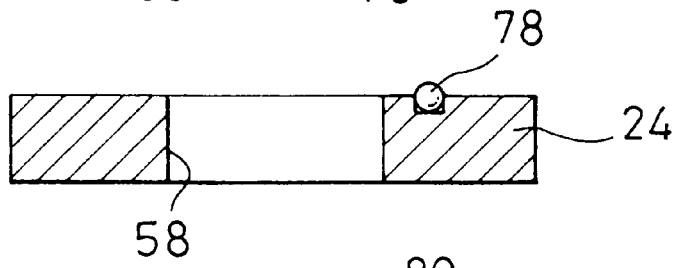
Figure 10C:
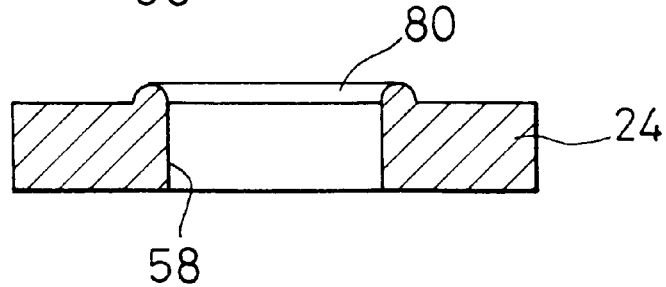

FIGS. 10A–10C show modified forms of the projection formed on the end plate 24. In the embodiment shown in FIG. 10A, an axial bore is formed through the end plate 24 at a position radially outwardly offset from the exhaust port 58, in which bore a pin 76 having a length slightly greater than the axial thickness of the end plate 24 is interference fitted. In the arrangement shown in FIG. 10B, a steel ball 78 is fixed within a cavity on the end plate 24 to form the projection. In the structure shown in FIG. 10C, an annular projection 80 adjacent to and surrounding the exhaust port 58 is integrally formed on the end plate 24.

FIGS. 11A–11C illustrate other embodiments of the vibrator wherein the projection is formed on the vibratory element 40.

In the embodiment of FIG. 11A, the vibratory element 40 is provided with a central bore in which a collar 82 having a length slightly longer than the axial thickness of the element 40 is press-fitted in such a manner as to protrude beyond the axial end faces of the element 40. The outer diameter of the collar 82 is selected to be greater than the inner diameter of the exhaust port 58 in order to preclude the vibratory element 40 from becoming in contact with the inner end wall 36 of the end plate 24 when the vibrator is not operated.

In the embodiment of FIG. 11B, the vibratory element 40 is formed with a central bore in which a steel ball 84 having a diameter slightly greater than the axial thickness of the element 40 is press-fitted. The exhaust port 58A is formed through the end plate 24 at a position radially outwardly offset from the axis of the plate.

In the embodiment of FIG. 11C, an insert 86 in the form of a short rod having a length slightly greater than the thickness of the vibratory element 40 is press-fitted in the central bore of the element 40.

Throughout these embodiments, the vibratory element 40 is prevented from adhering to the inner walls of the end plates 22 and 24 during the inoperative condition of the vibrator.

Figure 12:
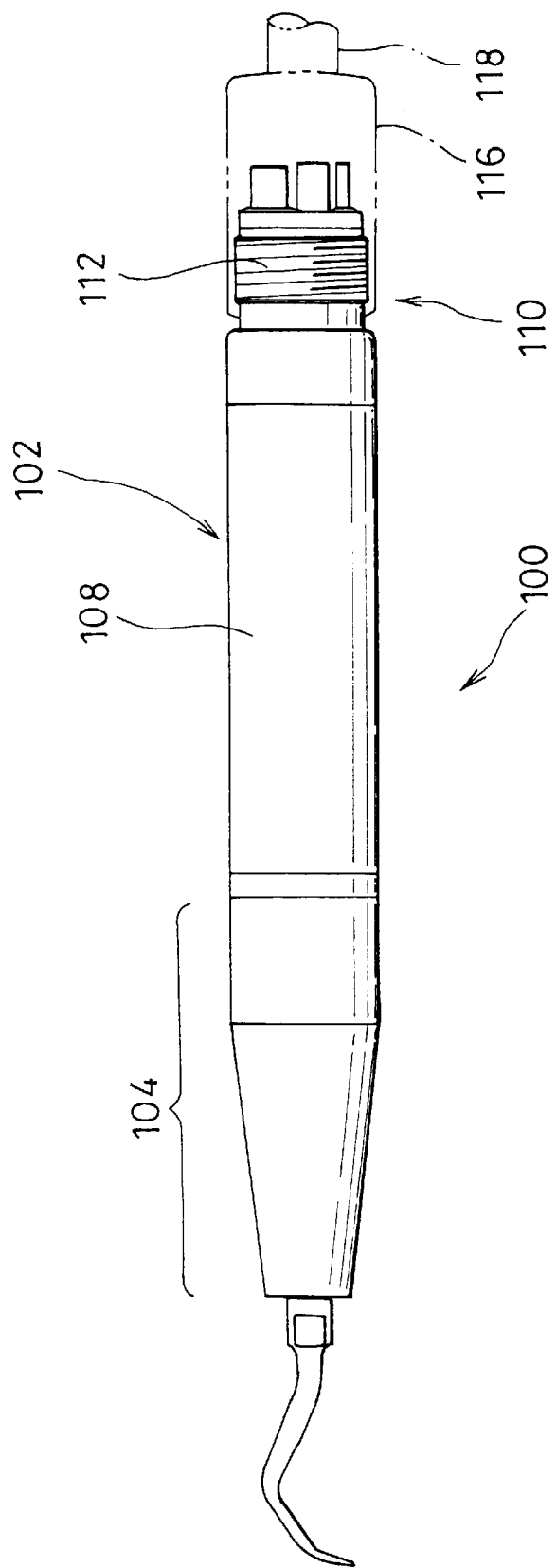
FIG. 12 is an enlarged elevational view showing a dental scaler incorporating another embodiment of the vibrator according to the invention.
Figure 13:
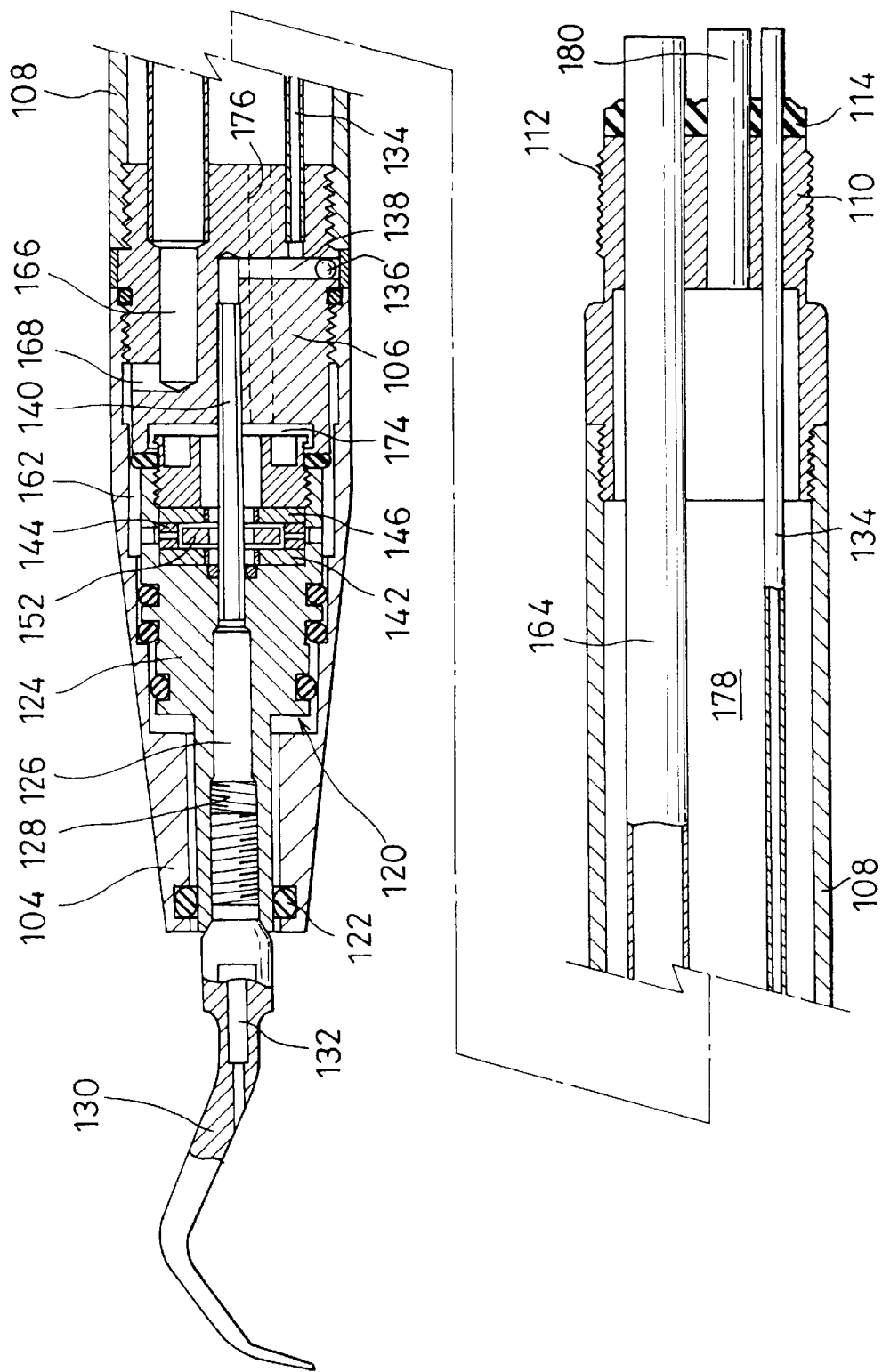
FIG. 13 is an enlarged axial cross-sectional view of the dental scaler shown in FIG. 12; and, FIG. 14 is an enlarged cross-sectional view of the vibrator shown in FIG. 13.
Figure 14:
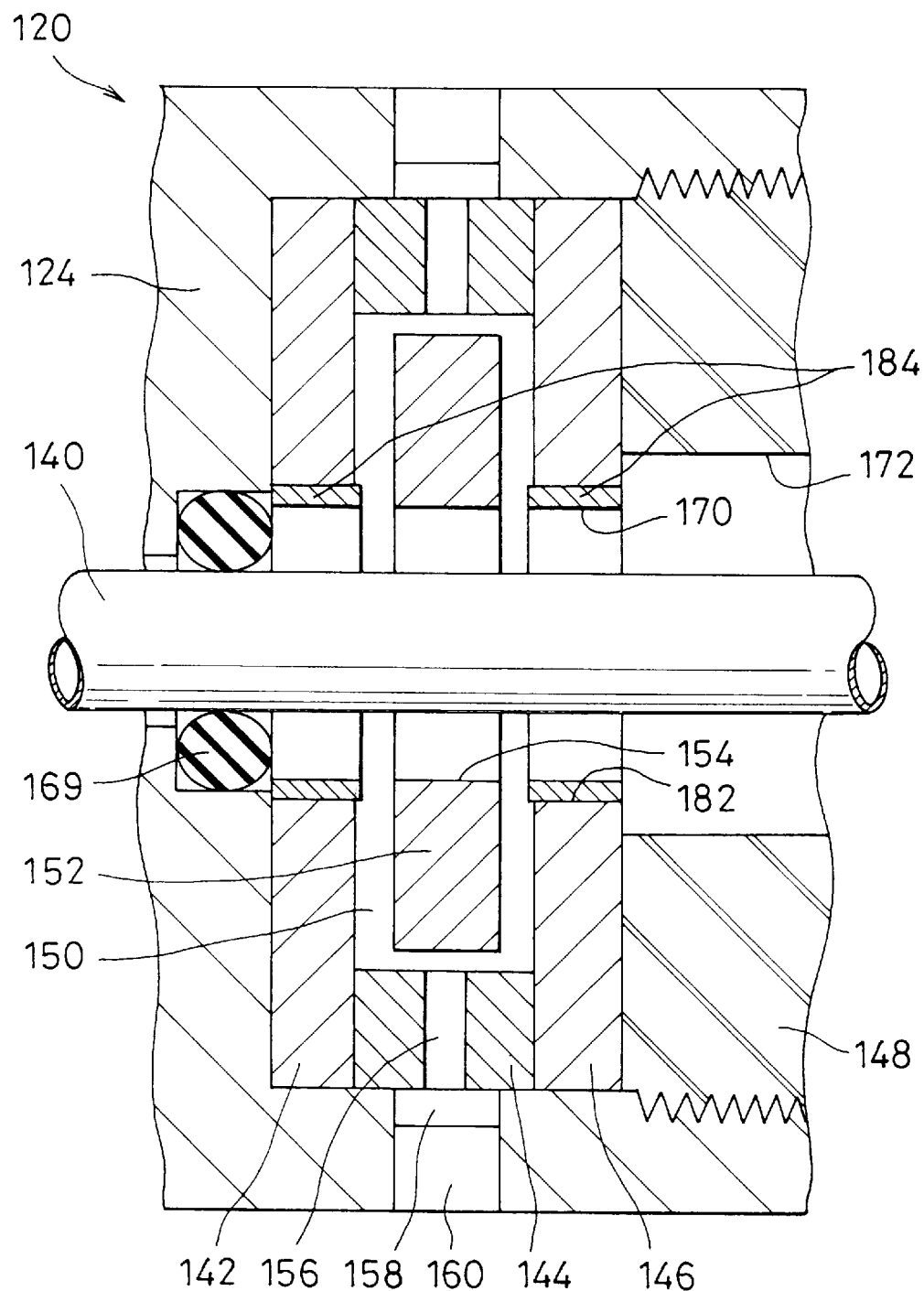

In FIGS. 12–14, there is shown a dental scaler wherein a vibrator according to another embodiment of the invention is incorporated. The dental scaler is designed and constructed in the form of an air-driven handpiece which is adapted to be connected through a dental hose to a conventional dental unit for a supply of compressed air.

Referring to FIGS. 12–14, the dental scaler 100 has an outer casing 102 adapted to be held by a hand. The outer casing 102 may include a frontal casing 104, a threaded joint fitting 106 screwed into the internal thread formed at the rear end of the frontal casing 104, a rear casing 108 screwed onto the external thread formed at the rear end of the joint 106, and a threaded end member 110 screwed into the internal thread at the rear end of the rear casing 108. The end member 110 is provided at its rear end with an external thread 112 which is adapted to be engaged by a conventional hose joint 116 for connecting the handpiece with a packing 114 to a dental hose 118 extending from a conventional dental unit, not shown.

A vibrator 120 according to the invention is accommodated within the frontal casing 104 and is located in the axial direction by screwing the joint fitting 106 into the frontal casing 104. The vibrator 120 is resiliently supported, and is isolated in vibration against the frontal casing 104 and the joint 106, by a plurality of elastomeric O-rings, only one of which is indicated in FIG. 13 by the reference numeral 122.

The vibrator 120 includes an outer casing 124 having a stepped bore 126 extending along the axis of the dental scaler 100. The frontal part of the bore 126 is formed with an internal thread 128 in which a threaded end of a scaling tool or tip 130 is detachably screwed.

The scaling tool 130 has a water passage 132 extending axially through the shank thereof for supplying water so as to cool the teeth and the scaling tool during scaling operation and to wash away removed debris. Water under pressure is supplied from the dental unit to the water passage 132 through a water pipe 134, a radial passage 138 in the joint 106 closed at the outer end by a ball plug 136, a water pipe 140, and the bore 126.

The vibrator 120 is similar in many respects to the embodiment shown in FIGS. 3–5. Referring primarily to the enlarged drawing of FIG. 14, the vibrator 120 is comprised of a disc-shaped end plate 142, an air injection ring 144, and a disc-shaped end plate 146, in a manner similar to the embodiment shown in FIGS. 3–5, these component parts being held together by a threaded retainer 148 screwed into the outer casing 124 to thereby form a working chamber 150. A disc-shaped vibratory element 152 is movably received in the working chamber 150. The vibratory element 152 is provided with a central bore 154 to ensure that the water pipe 140 does not interfere with the movement of the vibratory element 152.

It is desirable to make the vibrator 120 in as small size as possible in order to oscillate the scaling tool 130 at a high frequency of more than 6000 Hz. To this end, the axial size of the vibratory element 152 is preferably about 1–1.5 mm, with the outer diameter of the element 152 to be about 5–8 mm, the axial size of the working chamber 150 to be greater by about 0.5–1 mm than the axial size of the element 152, and the inner diameter of the chamber 150 to be greater by about 0.5–2 mm than the outer diameter of the element 152.

Tangentially directed air injection ports 156 of the injection ring 144 is communicated through an inner groove 158 of the outer casing 124 and radial ports 160 with an annular space 162 (FIG. 13) formed between the outer periphery of the outer casing 124 and the inner periphery of the frontal casing 104.

Compressed air from a dental unit is fed to the injection ring 144 through an air pipe 164, an axially extending air passage 166 formed in the joint fitting 106 at a position radially outwardly offset from the axis of the dental scaler, a radial passage 168 in the joint 106, and the annular space 162. An O-ring 169 tightly fitted between the water pipe 140 and the casing 124 serves to prevent air in the working chamber 150 from leaking forwardly thereof.

Used air in the working chamber 150 is delivered through an exhaust port 170 in the end plate 146 and a central port 172 in the retainer 148 to a space 174 formed between the retainer 148 and the joint 106, and is forwarded therefrom back to the dental unit through an axially extending exhaust passage 176 formed in the joint 106 at a position radially outwardly offset from the axis of the dental scaler, an inner space 178 in the rear casing 108, an exhaust pipe 180, and the dental hose 118.

The end plates 142 and 146 are made identical in order to provide a commonality of component parts. Therefore, only one of them will be described. Similar to the end plate 24 shown in FIGS. 3 and 4, the end plate 146 has a central bore 182 in which a collar 184 is press-fitted. A bore 170 in the collar 184 acts as an exhaust port for used air. The collar 184 has an outer diameter larger than the inner diameter of the vibratory element 152.

The inner end of the collar 184 protrudes slightly into the working chamber 150 beyond the inner end face of the end plate 146. In the case that the vibratory element 152 and the working chamber 150 are sized and dimensioned as described hereinbefore, it will be sufficient to prevent the vibratory element 152 from sticking to the end plate 146 during the inoperative state of the vibrator if the amount of projection of the inner end of the collar 184 as measured from the inner end face of the end plate 146 is equal to about 50 $\mu$m. With this amount of projection, the vibratory element would never interfere with the collar 184 during oscillation.

The end plates 142 and 146 and the associated collars 184 may be manufactured in a manner similar to that described with reference to the embodiment of FIGS. 3–5 and may be assembled in a similar manner.

As the mode of operation of the vibrator 120 is the same as that of the embodiment shown in FIGS. 3–6, description thereof would not be necessary. Vibration generated by the vibrator 120 is transmitted through the casing 124 to the scaling tool 130 to oscillate the tip of the tool 130 to remove calculus or plaque from the teeth.

When the dental scaler is not in use, the collars 184 slightly protruding from the inner end faces of the end plates 142 and 146 will preclude the vibratory element 152 from sticking to the end plates, as will be apparent from the foregoing description made with reference to FIG. 7. As a result, the vibratory element 152 will be again put into motion without fail as soon as the supply of compressed air is restarted.

The present inventor has made and tested a dental scaler as shown in FIGS. 12–14. The scaler was tested by intermittently operating the vibrator by interrupting air supply for 2 seconds for every 2 seconds of air supply. Throughout 23,400 cycles of intermittent operation, carried out for total 13 working hours, the vibratory element was restarted fully successfully, without causing sticking to the end plates.

Then, 50 sets of vibrators as shown in FIGS. 12–14 were made and each vibrator was tested for the quality of the vibratory element based on a judgment whether or not a sufficient magnitude of vibration was generated. The production yield of those vibratory elements having a good quality was calculated and was found to be about 82%. Obviously, this is an extremely high value as compared with the production yield of only about 19% obtained by the vibratory elements manufactured by the conventional method.

While the present invention has been described herein with reference to the specific embodiments thereof, it is contemplated that the present invention is not limited thereby and various changes and modifications may be made therein for those skilled in the art without departing from the scope of the invention. For example, the vibrators according to the invention may be used in any desired application other than dental scalers. The number of component parts of the vibrator, the structure and configuration of the vibrator, the position and arrangement of the air passages, and the number and angle of air injection ports may be modified as required.

I claim:

1. In a vibrator comprising a rigid body having a substantially disk-shaped working chamber defined by a cylindrical side wall and a pair of opposite end walls extending perpendicular to the axis of the chamber, a substantially disc-shaped vibratory element smaller in size than said chamber and received in said chamber for oscillatory movement, means for injecting a gaseous working fluid under pressure into said chamber in a direction tangential to said chamber to generate a swirling stream of working fluid therein, and, exhaust means for exhausting used working fluid out of said chamber, the improvement wherein axial end faces of said vibratory element are made substantially flat and wherein said body is provided with a projection protruding axially inwardly of at least one of said opposite end walls of said chamber to thereby prevent the vibratory element from sticking to said end wall when the vibrator is not operated.

2. A vibrator according to claim 1, wherein said body has an end plate defining at least one of said opposite end walls, said end plate having an axial bore extending therethrough, an insert member being securely inserted into said axial bore of said end plate, said insert member having an extension protruding axially inwardly of said end wall to thereby form said projection.

3. A vibrator according to claim 2, wherein said vibratory element has an axial bore extending therethrough along the axis thereof.

4. A vibrator according to claim 2, wherein said insert member is inserted into said axial bore of the end plate by press-fit.

5. A vibrator according to claim 4, wherein said axial bore and said insert member are coaxial with said body.

6. A vibrator according to claim 4, wherein said vibratory element has an axial bore extending therethrough along the axis thereof.

7. A vibrator according to claim 2, wherein said axial bore and said insert member are coaxial with said body.

8. A vibrator according to claim 7, wherein said insert member is in the form of a collar having an axial bore extending therethrough.

9. A vibrator according to claim 8, wherein said axial bore of said insert member serves to form part of said exhaust means.

10. A vibrator according to claim 9, wherein said extension of said collar is annular in form.

11. A vibrator according to claim 9, wherein said extension of said collar is partly cut out along the circumference thereof.

12. A vibrator according to claim 9, wherein said vibratory element has an axial bore extending therethrough along the axis thereof.

13. A vibrator according to claim 8, wherein said extension of said collar is annular in form.

14. A vibrator according to claim 13, wherein said vibratory element has an axial bore extending therethrough along the axis thereof.

15. A vibrator according to claim 8, wherein said extension of said collar is partly cut out along the circumference thereof.

16. A vibrator according to claim 8, wherein said vibratory element has an axial bore extending therethrough along the axis thereof.

17. A vibrator according to claim 7, wherein said vibratory element has an axial bore extending therethrough along the axis thereof.

18. A vibrator according to claim 1, wherein said vibratory element has an axial bore extending therethrough along the axis thereof.

19. In a vibrator comprising a rigid body having a substantially disk-shaped working chamber defined by a cylindrical side wall and a pair of opposite end walls extending perpendicular to the axis of the chamber, a substantially disc-shaped vibratory element smaller in size than said chamber and received in said chamber for oscillatory movement, means for injecting a gaseous working fluid under pressure into said chamber in a direction tangential to said chamber to generate a swirling stream of working fluid therein, and, exhaust means for exhausting used working fluid out of said chamber, the improvement wherein axial end faces of said vibratory element are machined substantially flat, said vibratory element having an axial bore extending therethrough along the axis thereof, an insert member protruding axially outwardly of said axial end faces of said vibratory element being securely inserted into said axial bore of the element to prevent the vibratory element from sticking to the end wall of the chamber when the vibrator is not operated.

20. A vibrator according to claim 19, wherein said insert member is in the form of a collar coaxial with said axial bore of the vibratory element.

* * * * *